United States Patent
Allen et al.

(10) Patent No.: US 6,583,337 B1
(45) Date of Patent: Jun. 24, 2003

(54) PLANT GLUCOSE-6-PHOSPHATE TRANSLOCATOR

(75) Inventors: Stephen M. Allen, Wilmington, DE (US); J. Antoni Rafalski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/436,521

(22) Filed: Nov. 9, 1999

Related U.S. Application Data
(60) Provisional application No. 60/107,910, filed on Nov. 10, 1998.

(51) Int. Cl.[7] ............... A01H 3/00; C07H 21/04; C07K 14/415; C12N 5/14; C12N 9/00
(52) U.S. Cl. ............... 800/278; 435/6; 435/69.1; 435/71.1; 435/183; 435/410; 435/419; 435/418; 435/252.3; 435/320.1; 530/350; 530/370; 536/23.1; 536/23.2; 536/23.6; 536/24.1; 536/24.3; 536/24.5
(58) Field of Search ............... 435/6, 69.1, 71.1, 435/183, 410, 419, 418, 252.3, 320.1; 530/370, 350; 536/23.1, 23.2, 23.6, 24.1, 24.3, 24.5

(56) References Cited

U.S. PATENT DOCUMENTS 5,945,509 A * 8/1999 Heinemann et al.

FOREIGN PATENT DOCUMENTS

WO    WO 95/16913    * 6/1995

OTHER PUBLICATIONS

Lazar et al. Molecular and Cellular Biology, vol. 8, No. 3, p. 1247–1252, Mar. 1988.*
Burgess et al. The Journal of Cell Biology, vol. 111 p. 2129–2138, 1990.*
Brown et al. Science, vol. 282, p. 131–133, Nov. 1998.*
Bork. Genome Research vol. 10, p. 398–400, 2000.*
Kammerer, B. et al. (1998) The Plant Cell 10:105–117.
Denyer et al. (1996) Plant Physiol. 112:779–785.
Thorbjornsen et al. (1996) Plant J. 10:243–250.
NCBI General Identifier No. 2997591.
NCBI General Identifier No. 2997589.

* cited by examiner

Primary Examiner—Phuong T. Bui

(57) ABSTRACT

This invention relates to an isolated nucleic acid fragment encoding a glucose-6-phosphate/phosphate translocator. The invention also relates to the construction of a chimeric gene encoding all or a portion of the glucose-6-phosphate/phosphate translocator, in sense or antisense orientation, wherein expression of the chimeric gene results in production of altered levels of the glucose-6-phosphate/phosphate translocator in a transformed host cell.

12 Claims, 2 Drawing Sheets

FIGURE 1A

```
SEQ ID NO:7   MIS-SLRQPSISISGSDVVLRKRHATLIQ------LRPQSFSPFSSREKSQRSVVSTK---
SEQ ID NO:2   MRAVSMAATHRRHRRTDGRLQHNTVTVTEEAGATIPAANMLAAAASVKLSTAGTATAPKM
SEQ ID NO:4   MIS-SLRQPVVGISGSDLLLRQRHATLI--------KARSFLPSLSREKGQRSLVSVQ---
SEQ ID NO:6   -----------------------------------------------------------
SEQ ID NO:8   MIP-SVRLSPGPAAFSGSSLRSKLPSI-------------PSISSLKPSKYVVSSL----

SEQ ID NO:7   ---KPLHLA-CLGVGNFGSVKN---------FESEASFGQSDLVK------CGAYEADR
SEQ ID NO:2   ALFKPLHLPPLFAAAAAAGPRPLSLSARPLYRQQDPLFLASRVASPAPPPSATADGAR
SEQ ID NO:4   ---KPLHIAASLGVGNFVSVKS---------DDDK----RGDLVK-----CEAYEADR
SEQ ID NO:6   ---------------------------------------R-------CSASAADD
SEQ ID NO:8   ---KPLYLAP-LDGPRTAELKS----------RRQPLEF------R-------CSASAADD

SEQ ID NO:7   SEVEGGD-GTPSEAAKKVKIGIYFATWALNVVFNIYNKKVLNAYPYPWLTSTLSLACGS
SEQ ID NO:2   PVEAAPAGAAPEEAARRAKIGVYFATWWALNVIFNIYNKKVLNAFPYPWLTSTLSLAAGS
SEQ ID NO:4   SEVEGA---STPSEAAKKVKIGIYFATWWALNVVFNIYNKKVLNAYPYPWLTSTLSLACGS
SEQ ID NO:6   ---TSSEAAQKLKISIYFATWWALNVIFNIYNKKVLNAFPYPWLTSTLSLACGS
SEQ ID NO:8   KESKTQVVPVQSEGAQRLKISIYFATWWALNVIFNIYNKKVLNAFPYPWLTSTLSLACGS

SEQ ID NO:7   LMMLISWATRIAEAPKTDLEFWKTLFPVAVAHTIGHVAATVSMSKVAVSFTHIIKSGEPA
SEQ ID NO:2   AIMLASWATRIAEAPATDLDFWKALSPVAIAHTIGHVAATVSMAKVAVSFTHIIKSGEPA
SEQ ID NO:4   LMMLISWATGIAEAPKTDPEFWKSLFPVAVAHTIGHVAATVSMSKVAVSFTHIIKSGEPA
SEQ ID NO:6   AMMLFSWWTCLVEAPKTDLDFWKALFPVAVAHTIGHVAATVSMSKVAVSFTHIIKSAEPA
SEQ ID NO:8   AMMLFSWATRLVEAPKTDLDFWKVLFPVAVAHTIGHVAATVSMSKVAVSFTHIIKSAEPA

SEQ ID NO:7   FSVLVSRFILGETFPVPVYLSLLPIIGGCALAAVTELNFNMIGFMGAMISNLAFVFRNIF
SEQ ID NO:2   FSVLVSRFFLGEHFPAPVYFSLLPIIGGCALAAITELNFNMIGFMGAMISNLAFVFRNIF
SEQ ID NO:4   FSVLVSRFLLGESFPVPVYLSLIPIIGGCALAAVTELNFNMIGFMGAMISNLAFVFRNIF
SEQ ID NO:6   FSVLVSRFILGESFPMPVYLSLLPIIGGCGLAAATELNFNMIGFMGAMISNLAFVFRNIF
SEQ ID NO:8   FSVLVSRFFLGETFPIPVYLSLLPIIGGCALAAVTELNFNMVGFMGAMISNLAFVFRNIF
```

FIGURE 1B

| | | |
|---|---|---|
| SEQ ID NO:7 | SKKGMKGKSVSGMNYYACLSILSLAILTPFAIAVEGPAMMAAGWQTALSEIGPQFIWWVA |
| SEQ ID NO:2 | SKKGMKGKSVSGMNYYACLSMLSLVILLPFAFAMEGPKVWAAGWQKAVAEIGPNFVWWVA |
| SEQ ID NO:4 | SKKGMKGKSVSGMNYYACLSILSLAILTPFAIAVEGPQMWAAGWQTAMSQIGPQFIWWLA |
| SEQ ID NO:6 | SKRGMKGKSVSGMNYYACLSIMSLIILAPFAIAMEGPQMWAAGWQKALADVGPNVLWWIG |
| SEQ ID NO:8 | SKRGMKGKSVSGMNYYACLSIMSLVILTPFAIAMEGPQMWAAGWQKALAEVGPNVVWWIA |
| | |
| SEQ ID NO:7 | AQSIFYHLYNQVSYMSLDEISPLTFSIGNTMKRISVIVSSIIIFHTPIQPVNALGAAIAV |
| SEQ ID NO:2 | AQSVFYHLYNQVSYMSLDEISPLTFSIGNTMKRISVIVASIIIFHTPVQPINALGAAIAI |
| SEQ ID NO:4 | AQSVFYHLYNQVSYMSLDQISPLTFSIGNTMKRISVIVSSIIIFHTPVQPINALGAAIAI |
| SEQ ID NO:6 | AQSVFYHLYNQVSYMSLDQISPLTFSIGNTMKRISVIVSSIIIFRTPVRPVNALGAAIAI |
| SEQ ID NO:8 | AQSVFYHLYNQVSYMSLDQISPLTFSIGNTMKRISVIVSSIIIFHTPVRAVNALGAAIAI |
| | |
| SEQ ID NO:7 | FGTFLYSQAKQ |
| SEQ ID NO:2 | LGTFIYSQAKQ |
| SEQ ID NO:4 | LGTFLYSQAKL |
| SEQ ID NO:6 | FGTFLYSQAKQ |
| SEQ ID NO:8 | LGTFLYSQAKA |

SEQUENCE LISTING

<160> NUMBER OF SEQ ID NOS: 8

<210> SEQ ID NO 1
<211> LENGTH: 1661
<212> TYPE: DNA
<213> ORGANISM: Oryza sativa

<400> SEQUENCE: 1

| | | | | | |
|---|---|---|---|---|---|
| gcacgagctt | acaaaagaag | gaaaaatgaa | tttaatgggc | ctgattcgag | cttgtgcatc | 60 |
| cgtgtaatta | cactatattg | tcggattgaa | gaagactcga | tgcgagcggt | ctctatggcc | 120 |
| gcaacccatc | gccgccatag | acgtacggac | ggccggctac | aacacaacac | agtaactgta | 180 |
| actgaagaag | ccggcgccac | cattcccgcc | gccaatatgc | tcgccgccgc | cgcctccgtc | 240 |
| aagctctcca | cggccgggac | cgccacggcg | cccaagatgg | cattattcaa | gcccctccac | 300 |
| ctccctcccc | tcttcgccgc | cgccgccgcc | gccgccgggc | cacgtcccct | ctccctctcg | 360 |
| gcgcgccccc | tgtaccggca | gcaggacccg | ttattcctgg | cgtcgcgcgt | cgcgtcaccg | 420 |
| gcgccgccgc | cgccgtccgc | caccgccgac | ggcgcccggc | cggtggaggc | tgcaccggcg | 480 |
| ggcgcggcgc | cggaggaggc | ggcgaggcgg | gccaagatcg | gggtctactt | cgcgacgtgg | 540 |
| tgggcgctga | acgtgatctt | caacatctac | aacaagaagg | tgctcaacgc | gttcccttac | 600 |
| ccgtggctca | cgtccacgct | ctccctcgcc | gccggctccg | ccatcatgct | cgcctcctgg | 660 |
| gccaccagga | tcgccgaggc | gcccgccacc | gacctcgatt | tctggaaggc | cctgtcaccg | 720 |
| gtggcgatcg | cgcacaccat | cgggcacgtg | gcggcgacgg | tgagcatggc | gaaggtggcg | 780 |
| gtgtcgttca | cccacatcat | caagagcggc | gagccggcgt | tcagcgtgct | cgtctccagg | 840 |
| ttcttcctcg | gcgagcactt | cccggcgccg | gtctacttct | ccctcctccc | aatcatcggc | 900 |
| ggatgcgccc | tcgccgccat | caccgagctc | aatttcaaca | tgattggatt | catggggggc | 960 |
| atgatctcga | acctggcatt | cgtgttccgg | aacatattct | ccaagaaggg | gatgaagggc | 1020 |
| aagtcggtga | gcgggatgaa | ctactacgcc | tgcctctcca | tgctctcgct | ggtcatcctc | 1080 |
| ctcccttttcg | ccttcgccat | ggagggggccc | aaggtgtggg | ctgccggctg | gcaaaaagcc | 1140 |
| gtcgccgaga | tcggtccaaa | cttcgtctgg | tgggtggcgg | cgcagagtgt | gttctaccac | 1200 |
| ttgtacaacc | aagtgtccta | catgtcattg | gacgagatct | caccactgac | attcagcatc | 1260 |
| ggcaacacca | tgaagcggat | ctccgtcatt | gtcgcctcca | tcatcatctt | ccacacgccg | 1320 |
| gtccagccca | tcaacgccct | cggagccgcc | attgcgattc | tcggaacttt | catctactct | 1380 |
| caggcgaagc | agtaatggca | taagcatgga | aatggcaccc | gttttcgcca | caagtcgcga | 1440 |
| ctcggtgctc | gggatgtaac | aatgctatga | gcatatatcc | aaggatccct | tgtaatatat | 1500 |
| tagatcttct | tttcttttca | ttttttctttc | tctaggtgta | gctgccaatg | tttcttctga | 1560 |
| attcgtcgag | ttccttgtact | atgactatga | tgatgtagag | aggtggatct | gcctaaataa | 1620 |
| agctgttaga | ttttttgcta | aaaaaaaaaa | aaaaaaaaaa | a | | 1661 |

```
<210> SEQ ID NO 2
<211> LENGTH: 464
<212> TYPE: PRT
<213> ORGANISM: Oryza sativa

<400> SEQUENCE: 2

Ala Arg Ala Tyr Lys Arg Arg Lys Asn Glu Phe Asn Gly Pro Asp Ser
  1               5                  10                  15

Ser Leu Cys Ile Arg Val Ile Thr Leu Tyr Cys Arg Ile Glu Glu Asp
             20                  25                  30

Ser Met Arg Ala Val Ser Met Ala Thr His Arg His Arg Arg
         35                  40                  45

Thr Asp Gly Arg Leu Gln His Asn Thr Val Thr Val Thr Glu Glu Ala
     50                  55                  60

Gly Ala Thr Ile Pro Ala Ala Asn Met Leu Ala Ala Ala Ser Val
 65                  70                  75                  80

Lys Leu Ser Thr Ala Gly Thr Ala Thr Ala Pro Lys Met Ala Leu Phe
                 85                  90                  95

Lys Pro Leu His Leu Pro Pro Leu Phe Ala Ala Ala Ala Ala Ala
                100                 105                 110

Gly Pro Arg Pro Leu Ser Leu Ser Ala Arg Pro Leu Tyr Arg Gln Gln
            115                 120                 125

Asp Pro Leu Phe Leu Ala Ser Arg Val Ala Ser Pro Ala Pro Pro Pro
    130                 135                 140

Pro Ser Ala Thr Ala Asp Gly Ala Arg Pro Val Glu Ala Ala Pro Ala
145                 150                 155                 160

Gly Ala Ala Pro Glu Glu Ala Ala Arg Arg Ala Lys Ile Gly Val Tyr
                165                 170                 175

Phe Ala Thr Trp Trp Ala Leu Asn Val Ile Phe Asn Ile Tyr Asn Lys
            180                 185                 190

Lys Val Leu Asn Ala Phe Pro Tyr Pro Trp Leu Thr Ser Thr Leu Ser
        195                 200                 205

Leu Ala Ala Gly Ser Ala Ile Met Leu Ala Ser Trp Ala Thr Arg Ile
    210                 215                 220

Ala Glu Ala Pro Ala Thr Asp Leu Asp Phe Trp Lys Ala Leu Ser Pro
225                 230                 235                 240

Val Ala Ile Ala His Thr Ile Gly His Val Ala Ala Thr Val Ser Met
                245                 250                 255

Ala Lys Val Ala Val Ser Phe Thr His Ile Ile Lys Ser Gly Glu Pro
            260                 265                 270

Ala Phe Ser Val Leu Val Ser Arg Phe Leu Gly Glu His Phe Pro
        275                 280                 285

Ala Pro Val Tyr Phe Ser Leu Leu Pro Ile Ile Gly Gly Cys Ala Leu
    290                 295                 300

Ala Ala Ile Thr Glu Leu Asn Phe Asn Met Ile Gly Phe Met Gly Ala
305                 310                 315                 320

Met Ile Ser Asn Leu Ala Phe Val Phe Arg Asn Ile Phe Ser Lys Lys
                325                 330                 335

Gly Met Lys Gly Lys Ser Val Ser Gly Met Asn Tyr Tyr Ala Cys Leu
            340                 345                 350

Ser Met Leu Ser Leu Val Ile Leu Pro Phe Ala Phe Ala Met Glu
        355                 360                 365

Gly Pro Lys Val Trp Ala Ala Gly Trp Gln Lys Ala Val Ala Glu Ile
    370                 375                 380
```

-continued

```
Gly Pro Asn Phe Val Trp Trp Val Ala Ala Gln Ser Val Phe Tyr His
385                 390                 395                 400

Leu Tyr Asn Gln Val Ser Tyr Met Ser Leu Asp Glu Ile Ser Pro Leu
                405                 410                 415

Thr Phe Ser Ile Gly Asn Thr Met Lys Arg Ile Ser Val Ile Val Ala
            420                 425                 430

Ser Ile Ile Ile Phe His Thr Pro Val Gln Pro Ile Asn Ala Leu Gly
        435                 440                 445

Ala Ala Ile Ala Ile Leu Gly Thr Phe Ile Tyr Ser Gln Ala Lys Gln
    450                 455                 460
```

<210> SEQ ID NO 3
<211> LENGTH: 1815
<212> TYPE: DNA
<213> ORGANISM: Glycine max
<220> FEATURE:
<221> NAME/KEY: unsure
<222> LOCATION: (1687)
<220> FEATURE:
<221> NAME/KEY: unsure
<222> LOCATION: (1701)
<220> FEATURE:
<221> NAME/KEY: unsure
<222> LOCATION: (1716)
<220> FEATURE:
<221> NAME/KEY: unsure
<222> LOCATION: (1808)

<400> SEQUENCE: 3

| | | | | | | |
|---|---|---|---|---|---|---|
| ctcgtgccgc | tcattgctgt | tcaccatttt | caattcattc | ctgtgttaga | ttccaagtgg | 60 |
| tttggtttgg | tttgacataa | ataaaccttt | caagatctca | gaggggcaga | agatcaaagc | 120 |
| caagacaaca | cactctcata | tataaaagag | tgtctctgat | aatttgatct | tgtttcttc | 180 |
| tctttctctc | ctttgagatt | tttcagcacc | ccaccaaggt | tttgtccgaa | aagcttgaat | 240 |
| ttttcgccta | cccttttacaa | tgatctcttc | attgagacaa | cctgttgtag | ggatcagtgg | 300 |
| ttctgatctt | cttttgaggc | aaagacatgc | aaccctaatt | aaggcaaggt | ccttttacc | 360 |
| ctctttgtca | agagaaaagg | gtcaagatc | tcttgtttca | gttcaaaagc | cacttcacat | 420 |
| tgctgcttct | cttggtgttg | gaaattttgt | gtcagtgaag | agtgatgatg | acaaaggggg | 480 |
| tgatttggtg | aagtgtgagg | cctatgaagc | agacagatca | gaggttgagg | gtgcaagcac | 540 |
| accatcagaa | gctgcaaaga | aggtgaaaat | tgggatatat | tttgcaacct | ggtgggcttt | 600 |
| gaatgtggtg | ttcaatattt | ataacaagaa | ggttttgaat | gcttaccctt | accccttggct | 660 |
| tacttcaact | ctctcacttg | catgtgggtc | tcttatgatg | ttgatctctt | gggccactgg | 720 |
| gattgctgaa | gccccaaaga | ctgatcctga | gttttggaag | tctttgttcc | ctgttgctgt | 780 |
| tgcacataca | attggacatg | tagcggcaac | agttagcatg | tcaaaagttg | cggtatcatt | 840 |
| cacacacatt | atcaagagtg | gtgaacctgc | ttttagtgtt | ctggtttcaa | gatttctttt | 900 |
| gggtgagagc | tttcctgtgc | cagtctatct | gtctttaatt | ccaatcattg | gtggatgtgc | 960 |
| acttgctgct | gtgactgagc | tcaatttcaa | tatgatcggt | tttatggggg | ccatgatatc | 1020 |
| gaatttggca | tttgtattcc | gtaatatctt | ttcgaaaaag | ggcatgaagg | gaaagtctgt | 1080 |
| tagtggaatg | aattactacg | catgtttatc | tattttatct | cttgctattc | tcacacccctt | 1140 |
| cgcaattgct | gtggaaggac | cgcaaatgtg | ggctgctgga | tggcaaacag | ccatgtctca | 1200 |
| aattggaccc | caattcatat | ggtggctagc | tgctcaaagt | gtattctatc | atctatacaa | 1260 |
| tcaagtgtca | tacatgtctc | tggatcagat | ctctcctttg | acgtttagca | ttggaaacac | 1320 |

```
catgaaacgt atatctgtca ttgtgtcttc cattattatc ttccacacac cagttcaacc   1380
catcaatgct cttggtgccg ccattgctat ccttggaacc ttcttgtatt cacaggcgaa   1440
actatagagt tggggaacta agattcctct agggacttgt ttgttacagt tcttcatgct   1500
caaccagcga caaggaagtt gattttgtaa tgtgtcactg ctggaatttt gtaatactag   1560
gatgatctgg ctatcagtcc atctgtagat ataataataa aaataatgct cctgaggaaa   1620
cattatcata atacagatta ttagggtttt tttttttttt tgaatttctg aaatgccaat   1680
gatttgnaaa taaaatgccc ntttggttta taatangtaa tgaagaaaga atttctcaag   1740
acattggtta ctataaaggg agccttgcaa taaaagtgat gcctaatgat caaatttgat   1800
gctccacnca cacac                                                   1815

<210> SEQ ID NO 4
<211> LENGTH: 395
<212> TYPE: PRT
<213> ORGANISM: Glycine max

<400> SEQUENCE: 4
```

Met Ile Ser Ser Leu Arg Gln Pro Val Val Gly Ile Ser Gly Ser Asp
  1               5                  10                  15

Leu Leu Arg Gln Arg His Ala Thr Leu Ile Lys Ala Arg Ser Phe
             20                  25                  30

Leu Pro Ser Leu Ser Arg Glu Lys Gly Gln Arg Ser Leu Val Ser Val
         35                  40                  45

Gln Lys Pro Leu His Ile Ala Ala Ser Leu Gly Val Gly Asn Phe Val
     50                  55                  60

Ser Val Lys Ser Asp Asp Lys Arg Gly Asp Leu Val Lys Cys Glu
 65                  70                  75                  80

Ala Tyr Glu Ala Asp Arg Ser Glu Val Glu Gly Ala Ser Thr Pro Ser
                 85                  90                  95

Glu Ala Lys Lys Val Lys Ile Gly Ile Tyr Phe Ala Thr Trp Trp
            100                 105                 110

Ala Leu Asn Val Val Phe Asn Ile Tyr Asn Lys Lys Val Leu Asn Ala
        115                 120                 125

Tyr Pro Tyr Pro Trp Leu Thr Ser Thr Leu Ser Leu Ala Cys Gly Ser
    130                 135                 140

Leu Met Met Leu Ile Ser Trp Ala Thr Gly Ile Ala Glu Ala Pro Lys
145                 150                 155                 160

Thr Asp Pro Glu Phe Trp Lys Ser Leu Phe Pro Val Ala Val Ala His
                165                 170                 175

Thr Ile Gly His Val Ala Ala Thr Val Ser Met Ser Lys Val Ala Val
            180                 185                 190

Ser Phe Thr His Ile Ile Lys Ser Gly Glu Pro Ala Phe Ser Val Leu
        195                 200                 205

Val Ser Arg Phe Leu Leu Gly Glu Ser Phe Pro Val Pro Val Tyr Leu
    210                 215                 220

Ser Leu Ile Pro Ile Ile Gly Gly Cys Ala Leu Ala Ala Val Thr Glu
225                 230                 235                 240

Leu Asn Phe Asn Met Ile Gly Phe Met Gly Ala Met Ile Ser Asn Leu
                245                 250                 255

Ala Phe Val Phe Arg Asn Ile Phe Ser Lys Lys Gly Met Lys Gly Lys
            260                 265                 270

Ser Val Ser Gly Met Asn Tyr Tyr Ala Cys Leu Ser Ile Leu Ser Leu

```
            275                 280                 285
Ala Ile Leu Thr Pro Phe Ala Ile Ala Val Glu Gly Pro Gln Met Trp
        290                 295                 300

Ala Ala Gly Trp Gln Thr Ala Met Ser Gln Ile Gly Pro Gln Phe Ile
305                 310                 315                 320

Trp Trp Leu Ala Ala Gln Ser Val Phe Tyr His Leu Tyr Asn Gln Val
                325                 330                 335

Ser Tyr Met Ser Leu Asp Gln Ile Ser Pro Leu Thr Phe Ser Ile Gly
            340                 345                 350

Asn Thr Met Lys Arg Ile Ser Val Ile Val Ser Ser Ile Ile Ile Phe
        355                 360                 365

His Thr Pro Val Gln Pro Ile Asn Ala Leu Gly Ala Ala Ile Ala Ile
    370                 375                 380

Leu Gly Thr Phe Leu Tyr Ser Gln Ala Lys Leu
385                 390                 395

<210> SEQ ID NO 5
<211> LENGTH: 1281
<212> TYPE: DNA
<213> ORGANISM: Triticum aestivum

<400> SEQUENCE: 5
gcacgagctc agaagcagca caaaagttga agatctcaat ctattttgcg acttggtggg     60
cgcttaatgt gatctttaac atctataaca agaaggttct caatgctttc ccgtatccct    120
ggctcacctc cacactatcc ctcgcctgtg ctcagcgat gatgctcttc tcatgggtca    180 cctgccagt gaggcccc aagactgact tagatttctg gaaagcactc ttcccggttg     240
ctgtggctca tacaattgga catgttgctg ccacagtgag catgtcaaag gtggcagtgt    300
cattcacaca cattatcaag agtgctgagc ctgcattcag tgttttggtg tcaaggttca    360
ttctcggaga gtcatttccg atgcctgtat atctttctct tctcccgatc attggtggtt    420
gtggtctagc tgctgcgaca gagctgaact ttaatatgat tggatttatg ggtgccatga    480
tatcgaacct tgcatttgtt ttccgcaaca tcttctcgaa gcggggcatg aaagggaagt    540
ctgtcagtgg catgaattac tacgcttgcc tttcaattat gtccctgatc atactcgcac    600
catttgctat tgctatggaa ggcccccaaa tgtgggccgc tggatggcaa aaggctcttg    660
cagatgttgg ccccaacgtt ctctggtgga ttggtgcaca gagcgttttc taccacctgt    720
ataaccaggt gtcctacatg tctttggacc agatttctcc attgacgttt agcattggca    780
atacaatgaa gcgcatatca gttattgttt cgtcaatcat tatcttccgt acacctgtcc    840
gccctgtaaa tgcactagga gctgccattg ccatctttgg cacattcctg tactctcagg    900
caaagcagtg aggtttaaac tattgttgaa ggtcaggttc atggacgaag aatgtctgca    960
gaaatagtac caagcagtgg ggcaaattt gcttgtgcaa gtgtcttgta gataaggtt    1020 taggttttca tgcgagaggc gataataata atggaccatg ttgctgtttc cttgttattt    1080
gttaaatcgc aaactgaact ccagtggcca tgaactgtcg ttgtatcctg aaataagaac    1140
tgcatggaaa ttcgtctgac agttccgttg ctggaaagta acgatagccc tgtgcttaac    1200
ggtaaattat tgatatttaa gaactttgtg ttaaaaaaaa aaaaaaaaaa aaaaaaaaaa    1260
aaaaaaaaaa aaaaaaaaa a                                              1281

<210> SEQ ID NO 6
<211> LENGTH: 302
<212> TYPE: PRT
```

<213> ORGANISM: Triticum aestivum

<400> SEQUENCE: 6

```
Thr Ser Ser Glu Ala Ala Gln Lys Leu Lys Ile Ser Ile Tyr Phe Ala
 1               5                  10                  15
Thr Trp Trp Ala Leu Asn Val Ile Phe Asn Ile Tyr Asn Lys Lys Val
                20                  25                  30
Leu Asn Ala Phe Pro Tyr Pro Trp Leu Thr Ser Thr Leu Ser Leu Ala
             35                  40                  45
Cys Gly Ser Ala Met Met Leu Phe Ser Trp Val Thr Cys Leu Val Glu
         50                  55                  60
Ala Pro Lys Thr Asp Leu Asp Phe Trp Lys Ala Leu Phe Pro Val Ala
 65                  70                  75                  80
Val Ala His Thr Ile Gly His Val Ala Thr Val Ser Met Ser Lys
                 85                  90                  95
Val Ala Val Ser Phe Thr His Ile Ile Lys Ser Ala Glu Pro Ala Phe
                100                 105                 110
Ser Val Leu Val Ser Arg Phe Ile Leu Gly Glu Ser Phe Pro Met Pro
                115                 120                 125
Val Tyr Leu Ser Leu Leu Pro Ile Ile Gly Gly Cys Gly Leu Ala Ala
    130                 135                 140
Ala Thr Glu Leu Asn Phe Asn Met Ile Gly Phe Met Gly Ala Met Ile
145                 150                 155                 160
Ser Asn Leu Ala Phe Val Phe Arg Asn Ile Phe Ser Lys Arg Gly Met
                165                 170                 175
Lys Gly Lys Ser Val Ser Gly Met Asn Tyr Tyr Ala Cys Leu Ser Ile
                180                 185                 190
Met Ser Leu Ile Ile Leu Ala Pro Phe Ala Ile Ala Met Glu Gly Pro
            195                 200                 205
Gln Met Trp Ala Ala Gly Trp Gln Lys Ala Leu Ala Asp Val Gly Pro
    210                 215                 220
Asn Val Leu Trp Trp Ile Gly Ala Gln Ser Val Phe Tyr His Leu Tyr
225                 230                 235                 240
Asn Gln Val Ser Tyr Met Ser Leu Asp Gln Ile Ser Pro Leu Thr Phe
                245                 250                 255
Ser Ile Gly Asn Thr Met Lys Arg Ile Ser Val Ile Val Ser Ser Ile
                260                 265                 270
Ile Ile Phe Arg Thr Pro Val Arg Pro Val Asn Ala Leu Gly Ala Ala
            275                 280                 285
Ile Ala Ile Phe Gly Thr Phe Leu Tyr Ser Gln Ala Lys Gln
    290                 295                 300
```

<210> SEQ ID NO 7
<211> LENGTH: 401
<212> TYPE: PRT
<213> ORGANISM: Pisum sativum

<400> SEQUENCE: 7

```
Met Ile Ser Ser Leu Arg Gln Pro Ser Ile Ser Ile Ser Gly Ser Asp
 1               5                  10                  15
Val Val Leu Arg Lys Arg His Ala Thr Leu Ile Gln Leu Arg Pro Gln
                20                  25                  30
Ser Phe Ser Pro Phe Ser Ser Arg Glu Lys Ser Gln Arg Ser Val Val
             35                  40                  45
Ser Thr Lys Lys Pro Leu His Leu Ala Cys Leu Gly Val Gly Asn Phe
```

|   |   |   |   |   |   |   |   |   |   |   |
|---|---|---|---|---|---|---|---|---|---|---|
| | | | 50 | | | 55 | | | 60 | |
| Gly | Ser | Val | Lys | Asn | Phe | Glu | Ser | Glu | Ala | Ser | Phe | Gly | Gln | Ser | Asp |
| 65 | | | | 70 | | | | 75 | | | | | | | 80 |
| Leu | Val | Lys | Cys | Gly | Ala | Tyr | Glu | Ala | Asp | Arg | Ser | Glu | Val | Glu | Gly |
| | | | | 85 | | | | | 90 | | | | | 95 | |
| Gly | Asp | Gly | Thr | Pro | Ser | Glu | Ala | Ala | Lys | Lys | Val | Lys | Ile | Gly | Ile |
| | | | | 100 | | | | | 105 | | | | | 110 | |
| Tyr | Phe | Ala | Thr | Trp | Trp | Ala | Leu | Asn | Val | Val | Phe | Asn | Ile | Tyr | Asn |
| | | | 115 | | | | | 120 | | | | | 125 | | |
| Lys | Lys | Val | Leu | Asn | Ala | Tyr | Pro | Tyr | Pro | Trp | Leu | Thr | Ser | Thr | Leu |
| | 130 | | | | | 135 | | | | | 140 | | | | |
| Ser | Leu | Ala | Cys | Gly | Ser | Leu | Met | Met | Leu | Ile | Ser | Trp | Ala | Thr | Arg |
| 145 | | | | | 150 | | | | | 155 | | | | | 160 |
| Ile | Ala | Glu | Ala | Pro | Lys | Thr | Asp | Leu | Glu | Phe | Trp | Lys | Thr | Leu | Phe |
| | | | | 165 | | | | | 170 | | | | | 175 | |
| Pro | Val | Ala | Val | Ala | His | Thr | Ile | Gly | His | Val | Ala | Ala | Thr | Val | Ser |
| | | | | 180 | | | | | 185 | | | | | 190 | |
| Met | Ser | Lys | Val | Ala | Val | Ser | Phe | Thr | His | Ile | Ile | Lys | Ser | Gly | Glu |
| | | | 195 | | | | | 200 | | | | | 205 | | |
| Pro | Ala | Phe | Ser | Val | Leu | Val | Ser | Arg | Phe | Ile | Leu | Gly | Glu | Thr | Phe |
| | 210 | | | | | 215 | | | | | 220 | | | | |
| Pro | Val | Pro | Val | Tyr | Leu | Ser | Leu | Leu | Pro | Ile | Ile | Gly | Gly | Cys | Ala |
| 225 | | | | | 230 | | | | | 235 | | | | | 240 |
| Leu | Ala | Ala | Val | Thr | Glu | Leu | Asn | Phe | Asn | Met | Ile | Gly | Phe | Met | Gly |
| | | | | 245 | | | | | 250 | | | | | 255 | |
| Ala | Met | Ile | Ser | Asn | Leu | Ala | Phe | Val | Phe | Arg | Asn | Ile | Phe | Ser | Lys |
| | | | 260 | | | | | 265 | | | | | 270 | | |
| Lys | Gly | Met | Lys | Gly | Lys | Ser | Val | Ser | Gly | Met | Asn | Tyr | Tyr | Ala | Cys |
| | | 275 | | | | | 280 | | | | | 285 | | | |
| Leu | Ser | Ile | Leu | Ser | Leu | Ala | Ile | Leu | Thr | Pro | Phe | Ala | Ile | Ala | Val |
| 290 | | | | | 295 | | | | | 300 | | | | | |
| Glu | Gly | Pro | Ala | Met | Trp | Ala | Ala | Gly | Trp | Gln | Thr | Ala | Leu | Ser | Glu |
| 305 | | | | | 310 | | | | | 315 | | | | | 320 |
| Ile | Gly | Pro | Gln | Phe | Ile | Trp | Trp | Val | Ala | Ala | Gln | Ser | Ile | Phe | Tyr |
| | | | | 325 | | | | | 330 | | | | | 335 | |
| His | Leu | Tyr | Asn | Gln | Val | Ser | Tyr | Met | Ser | Leu | Asp | Glu | Ile | Ser | Pro |
| | | | 340 | | | | | 345 | | | | | 350 | | |
| Leu | Thr | Phe | Ser | Ile | Gly | Asn | Thr | Met | Lys | Arg | Ile | Ser | Val | Ile | Val |
| | | 355 | | | | | 360 | | | | | 365 | | | |
| Ser | Ser | Ile | Ile | Ile | Phe | His | Thr | Pro | Ile | Gln | Pro | Val | Asn | Ala | Leu |
| | 370 | | | | | 375 | | | | | 380 | | | | |
| Gly | Ala | Ala | Ile | Ala | Val | Phe | Gly | Thr | Phe | Leu | Tyr | Ser | Gln | Ala | Lys |
| 385 | | | | | 390 | | | | | 395 | | | | | 400 |
| Gln | | | | | | | | | | | | | | | |

<210> SEQ ID NO 8
<211> LENGTH: 387
<212> TYPE: PRT
<213> ORGANISM: Zea mays

<400> SEQUENCE: 8

|   |   |   |   |   |   |   |   |   |   |   |
|---|---|---|---|---|---|---|---|---|---|---|
| Met | Ile | Pro | Ser | Val | Arg | Leu | Ser | Pro | Gly | Pro | Ala | Ala | Phe | Ser | Gly |
| 1 | | | | 5 | | | | | 10 | | | | | 15 | |
| Ser | Ser | Leu | Arg | Ser | Lys | Leu | Pro | Ser | Ile | Pro | Ser | Ile | Ser | Ser | Leu |

-continued

```
                   20                  25                  30
Lys Pro Ser Lys Tyr Val Val Ser Ser Leu Lys Pro Leu Tyr Leu Ala
            35                  40                  45
Pro Leu Asp Gly Pro Arg Thr Ala Glu Leu Lys Ser Arg Arg Gln Pro
 50                  55                  60
Leu Glu Phe Arg Cys Ser Ala Ser Ala Ala Asp Asp Lys Glu Ser Lys
 65                  70                  75                  80
Thr Gln Val Val Pro Val Gln Ser Glu Gly Ala Gln Arg Leu Lys Ile
             85                  90                  95
Ser Ile Tyr Phe Ala Thr Trp Trp Ala Leu Asn Val Ile Phe Asn Ile
            100                 105                 110
Tyr Asn Lys Lys Val Leu Asn Ala Phe Pro Tyr Pro Trp Leu Thr Ser
            115                 120                 125
Thr Leu Ser Leu Ala Cys Gly Ser Ala Met Met Leu Phe Ser Trp Ala
130                 135                 140
Thr Arg Leu Val Glu Ala Pro Lys Thr Asp Leu Asp Phe Trp Lys Val
145                 150                 155                 160
Leu Phe Pro Val Ala Val Ala His Thr Ile Gly His Val Ala Ala Thr
                165                 170                 175
Val Ser Met Ser Lys Val Ala Val Ser Phe Thr His Ile Ile Lys Ser
                180                 185                 190
Ala Glu Pro Ala Phe Ser Val Leu Val Ser Arg Phe Phe Leu Gly Glu
            195                 200                 205
Thr Phe Pro Ile Pro Val Tyr Leu Ser Leu Leu Pro Ile Ile Gly Gly
            210                 215                 220
Cys Ala Leu Ala Ala Val Thr Glu Leu Asn Phe Asn Met Val Gly Phe
225                 230                 235                 240
Met Gly Ala Met Ile Ser Asn Leu Ala Phe Val Phe Arg Asn Ile Phe
                245                 250                 255
Ser Lys Arg Gly Met Lys Gly Lys Ser Val Ser Gly Met Asn Tyr Tyr
                260                 265                 270
Ala Cys Leu Ser Ile Met Ser Leu Val Ile Leu Thr Pro Phe Ala Ile
            275                 280                 285
Ala Met Glu Gly Pro Gln Met Trp Ala Ala Gly Trp Gln Lys Ala Leu
 290                 295                 300
Ala Glu Val Gly Pro Asn Val Val Trp Trp Ile Ala Ala Gln Ser Val
305                 310                 315                 320
Phe Tyr His Leu Tyr Asn Gln Val Ser Tyr Met Ser Leu Asp Gln Ile
                325                 330                 335
Ser Pro Leu Thr Phe Ser Ile Gly Asn Thr Met Lys Arg Ile Ser Val
            340                 345                 350
Ile Val Ser Ser Ile Ile Ile Phe His Thr Pro Val Arg Ala Val Asn
            355                 360                 365
Ala Leu Gly Ala Ala Ile Ala Ile Leu Gly Thr Phe Leu Tyr Ser Gln
 370                 375                 380
Ala Lys Ala
385
```

US 6,583,337 B1

PLANT GLUCOSE-6-PHOSPHATE TRANSLOCATOR

This application claims priority benefit to U.S. Provisional Application No. 60/107,910 filed Nov. 10, 1998, now abandoned.

FIELD OF THE INVENTION

This invention is in the field of plant molecular biology. More specifically, this invention pertains to nucleic acid fragments encoding glucose-6-phosphate/phosphate translocators in plants and seeds.

BACKGROUND OF THE INVENTION

During $C_3$ photosynthesis, energy from solar radiation is used for the formation of phosphorylated C3 sugar phosphates, triose phosphates (triosP), and 3-phosphoglycerate (3-PGA). These products are then exported from the chloroplasts into the cytosol via the trioseP/3-PGA/phosphate translocator (TPT). In the mature leaves of most plants, the exported photosynthates are then used in the formation of sucrose, which is allocated via the phloem to the heterotrophic plant organs, such as young leaves, roots, seeds, fruits or tubers. In these sink tissues, sucrose serves as a source of carbon and energy and is first cleaved by the action of invertases or sucrose synthase. The products of these reactions are converted into hexose phosphates.

Nongreen plastids of heterotrophic tissues import carbohydrates to fuel metabolism in those cells. Amyloplasts, found in storage tissues, convert the carbohydrates into starch which is efficiently stored. In general, the plastids of heterotrophic tissues cannot generate hexose phosphates from C3 compounds due to an absence of fructose 1,6-bisphosphatase activity. Thus, the TPTs that transported the triose-phosphates out of the chloroplasts in photosynthetic tissues are not useful for transporting them back into the storage plastids of heterotrophic tissues. Therefore, nongreen plastids rely on the import of hexose phosphates to supply the materials for starch biosynthesis, and for generating energy through the oxidative pentose phosphate pathway. A hexose-phosphate/phosphate translocator (or transporter, or antiporter, which are used interchangeably herein) allows membrane passage of hexose-phosphate while simultaneously transporting inorganic phosphate, or triose-phosphates, in the opposite direction. In nongreen plant tissues glucose 6-phosphate (Glc6P) is the preferred hexose phosphate taken up by nonphotosynthetic plastids. The translocation event is selective, as shown by the inability of amyloplast membranes to transport phosphoenolpyruvate, fructose-6-phosphate, or glucose-1-phosphate. It has been shown recently (Kammerer, B. et al. (1998) *The Plant Cell* 10:105–117) that Glc6P is taken up by nongreen plastids via a glucose-6-phosphate/phosphate translocator (GP/PT). Glucose-6-phosphate imported by the GP/PT protein can be incorporated into starch, releasing inorganic phosphate, or can serve as a substrate for the oxidative pentose phosphate pathway, yielding triose phosphates.

GP/PT is one of the main translocators to provide plastids with carbon for biosynthetic pathways and energy. GP/PT transcripts are abundant in heterotrophic tissues active in starch synthesis, such as potato tubers, maize kernels, and pea roots (Kammerer et al. (1998) *Plant Cell* 10:105–117), but are barely detectable in photosynthetic tissues. However, endosperm-specific starch synthesis, found in maize and barley, occurs in the cytosol and does not utilize GP/PT transport (Denyer et al. (1996) Plant Physiol 112:779–185; Thorbjornsen et al. (1996) Plant J 10:243–250). So not all starch containing tissues are necessarily dependent upon GP/PT activities. Still, it is clear that GP/PTs play an integral role in maintaining starch synthesis and energy metabolism in normal plant growth and development. Accordingly, the availability of nucleic acid sequences encoding all or a portion of the GP/PT protein would facilitate studies to better understand hexose phosphate transport, provide genetic tools for the manipulation of biosynthetic pathways and energy production, and may provide possible targets for herbicides or the engineering of herbicide resistance.

SUMMARY OF THE INVENTION

The present invention relates to isolated polynucleotides comprising a nucleotide sequence encoding a first polypeptide of at least 401 amino acids that has at least 70% identity based on the Clustal method of alignment when compared to a rice glucose-6-phosphate/phosphate translocator (GP/PT) polypeptide of SEQ ID NO:2, a nucleotide sequence encoding a first polypeptide of at least 395 amino acids that has at least 86% identity based on the Clustal method of alignment when compared to a soybean GP/PT polypeptide of SEQ ID NO:4, and a nucleotide sequence encoding a first polypeptide of at least 302 amino acids that has at least 93% identity based on the Clustal method of alignment when compared to a wheat GP/PT polypeptide of SEQ ID NO:6. The present invention also relates to an isolated polynucleotide comprising the complement of the nucleotide sequences described above.

It is preferred that the isolated polynucleotides of the claimed invention consists of a nucleic acid sequence selected from the group consisting of SEQ ID NOs:1, 3, and 5, that codes for the polypeptide selected from the group consisting of SEQ ID NOs:2, 4, and 6. The present invention also relates to an isolated polynucleotide comprising a nucleotide sequences of at least one of 60 (preferably at least one of 40, most preferably at least 30) contiguous nucleotides derived from a nucleotide sequence selected from the group consisting of SEQ ID NOs:1, 3, and 5, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a GP/PT polypeptide of at least 401 amino acids that has at least 70% identity based on the Clustal method of alignment when compared to a glucose-6-phosphate/phosphate translocator polypeptide of SEQ ID NO:2, a GP/PT polypeptide of at least 395 amino acids that has at least 86% identity based on the Clustal method of alignment when compared to a glucose-6-phosphate/phosphate translocator polypeptide of SEQ ID NO:4, and a composition consisting of a GP/PTpolypeptide of at least 302 amino acids that has at least 93% identity based on the Clustal method of alignment when compared to a glucose-6-phosphate/phosphate translocator polypeptide of SEQ ID NO:6.

The present invention relates to a method of selecting an isolated polynucleotide that affects the level of expression of a GP/PT polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a GP/PT polypeptide in the host cell containing the isolated polynucleotide; and comparing the level of a GP/PT polypeptide in the host cell containing the isolated polynucleotide with the level of a GP/PT polypeptide in a host cell that does not contain the isolated polynucleotide.

The present invention relates to a method of obtaining a nucleic acid fragment encoding a substantial portion of a GP/PT polypeptide gene, preferably a plant GP/PT polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, and 5 and the complement of such nucleotide sequences; and amplifying a nucleic acid fragment (preferably a cDNA inserted in a cloning vector) using the oligonucleotide primer. The amplified nucleic acid fragment preferably will encode a portion of a GP/PT amino acid sequence.

The present invention also relates to a method of obtaining a nucleic acid fragment encoding all or a substantial portion of the amino acid sequence encoding a GP/PT polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a GP/PT, the method comprising the steps of: (a) transforming a host cell with a chimeric gene comprising a nucleic acid fragment encoding a GP/PT, operably linked to suitable regulatory sequences; (b) growing the transformed host cell under conditions that are suitable for expression of the chimeric gene wherein expression of the chimeric gene results in production of GP/PT in the transformed host cell; (c) optionally purifying the GP/PT expressed by the transformed host cell; (d) treating the GP/PT with a compound to be tested; and (e) comparing the activity of the GP/PT that has been treated with a test compound to the activity of an untreated GP/PT, thereby selecting compounds with potential for inhibitory activity.

The present invention relates to a composition comprising an isolated polynucleotide of the present invention.

The present invention relates to an isolated polynucleotide comprising at least one of 30 contiguous nucleotides of a nucleic acid sequence selected from the group consisting of SEQ ID NOs:1, 3, 5 and the complement of such sequences.

The present invention relates to an expression cassette comprising an isolated polynucleotide of the present invention operably linked to a promoter.

The present invention relates to a method for positive selection of a transformed cell comprising:
(a) transforming a plant cell with a chimeric gene of claim 5 or an expression cassette of the present invention; and
(b) growing the transformed plant cell, wherein the plant cell is a monocot or a dicot such as rice, soybean or wheat, under conditions allowing expression of the polynucleotide in an amount sufficient to complement a glucose-6-phosphate/phosphate translocator auxotroph to provide a positive selection means.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A and 1B show a comparison of the amino acid sequences of the rice (r10n.pk0016.f6:fis), soybean (soycon, a contig of sequences listed in Table 3), and wheat (wr1.pk0053.e6) GP/PT (SEQ ID NOs:2, 4, and 6) versus the pea (SEQ ID NO:7) and the corn (SEQ ID NO:8) proteins. The rice amino acid sequence is presented from the first methionine in the sequence, however there is an in-frame 33 amino acid leader attached to this polypeptide (amino acids 1–33 of SEQ ID NO:2). The wheat sequence represents a truncated cDNA clone that starts approximately at the amino-terminal end of the mature protein.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Glucose-6-Phosphate/Phosphate Translocators

| Protein | Clone Designation | SEQ ID NO: (Nucleotide) | SEQ ID NO: (Amino Acid) |
|---|---|---|---|
| Rice GP/PT (*Oryza sativa*) | r10n.pk0016.f6:fis | 1 | 2 |
| Soybean GPIPT (*Glycine max*) | Contig of: s2.07c09 sde4c.pk0001.g4 sdp4c.pk003.o9 se4.pk0005.e7 sgs3c.pk001.i5 sl1.pk0058.a8 sl2.pk0047.b3 sls2c.pk013.b10 sr1.pk0007.d2 src3c.pk020.e1 | 3 | 4 |
| Wheat GP/PT (*Triticum sp.*) | wr1.pk0053.e6:fis | 5 | 6 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least one of 60 contiguous nucleotides, preferably at least one of 40 contiguous nucleotides, most preferably one of at least 30 contiguous nucleotides, of the nucleic acid sequence of the SEQ ID NOs:1, 3, and 5.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, and 5, and the complement of such nucleotide sequences may be used in methods of selecting an isolated polynucleotide that affects the expression of a polypeptide in a plant cell. A method of selecting an isolated polynucleotide that affects the level of expression of a polypeptide (such as GP/PT polypeptide) in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several glucose-6-phosphate/phosphate translocator have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other GP/PT, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, and 5 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as GP/PT) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, and 5, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of sugars, starches, and metabolites in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences.

Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded glucose-6-phosphate/phosphate translocator. An example of a vector for high level expression of the instant polypeptides in a bacterial host is provided (Example 6).

Additionally, the instant polypeptides can be used as a targets to facilitate design and/or identification of inhibitors of those enzymes that may be useful as herbicides. This is desirable because the polypeptides described herein catalyze the transport of glucose-6-phosphate into the plastid. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various rice, soybean, or corn tissues were prepared. The characteristics of the libraries are described below.

TABLE 2 cDNA Libraries from Rice, Soybean, and Wheat

| Library | Tissue | Clone |
|---|---|---|
| r10n | Rice 15 day old leaf* | r10n.pk0016.f6:fis |
| s2 | Soybean Seed, 19 Days After Flowering | s2.07c09 |
| sde4c | Soybean Developing Embryo (9–11 mm) | sde4c.pk0001.g4 |
| sdp4c | Soybean Developing Pods (10–12 mm) | sdp4c.pk003.o9 |
| se4 | Soybean embryo, 19 days after flowering | se4.pk0005.e7 |
| sgs3c | Soybean Seeds 25 Hours After Germination | sgs3c.pk001.i5 |

TABLE 2-continued cDNA Libraries from Rice, Soybean, and Wheat

| Library | Tissue | Clone |
|---|---|---|
| sl1 | Soybean Two-Week-Old Developing Seedlings | sl1.pk0058.a8 |
| sl2 | Soybean Two-Week-Old Developing Seedlings Treated With 2.5 ppm chlorimuron | sl2.pk0047.b3 |
| sls2c | Soybean Infected With *Sclerotinia sclerotiorum* mycelium | sls2c.pk013.b10 |
| sr1 | Soybean Root | sr1.pk0007.d2 |
| src3c | Soybean 8 Day Old Root Infected With Cyst Nematode | src3c.pk020.e1 |
| wr1 | Wheat root from 7 day old seedling | wr1.pk0053.e6:fis |

*This library was normalized essentially as described in U.S. Pat. No. 5,482,845, incorporated hereby by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding glucose-6-phosphate/phosphate translocators were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Glucose-6-Phosphate/Phosphate Translocator The BLASTX search using the EST sequences from clones listed in Table 3 revealed similarity of the polypeptides encoded by the cDNAs to GP/PT from pea and corn (NCBI Accession No. gi 2997591 and gi 2997589, respectively). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to GP/PT

| Clone | Status | BLAST pLog Score 2997591 |
|---|---|---|
| r10n.pk0016.f6:fis | FIS | 155.00 |
| Contig of: | Contig | 254.00 |
| s2.07c09 | | |
| sde4c.pk0001.g4 | | |
| sdp4c.pk003.o9 | | |
| se4.pk0005.e7 | | |
| sgs3c.pk001.i5 | | |
| sl1.pk0058.a8 | | |
| sl2.pk0047.b3 | | |
| sls2c.pk013.b10 | | |
| sr1.pk0007.d2 | | |
| src3c.pk020.e1 | | |

| Clone | Status | BLAST pLog Score 2997589 |
|---|---|---|
| wr1.pk0053.e6:fis | FIS | 162.00 |

FIG. 1 presents an alignment of the amino acid sequences set forth in SEQ ID NOs:2, 4, and 6, and the pea sequence (SEQ ID NO:7), and the corn sequence (SEQ ID NO:8). The data in Table 4 represents a calculation of the percent identity of the amino acid sequences set forth in SEQ ID NOs:2, 4, and the pea sequence (SEQ ID NO:7), and the amino acid sequences set forth in SEQ ID NO:6 and the corn sequence (SEQ ID NO:8).

TABLE 4

Percent Identity of Amino Acid Sequences Deduced From the Nucleotide Sequences of cDNA Clones Encoding Polypeptides Homologous to GP/PT

| SEQ ID NO. | Percent Identity to 2997591 |
|---|---|
| 2 | 67.3% |
| 4 | 85.3% |

| SEQ ID NO. | Percent Identity to 2997589 |
|---|---|
| 6 | 92.7% |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a GP/PT. These sequences represent the first rice, soybean, and wheat sequences encoding GP/PT.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the P subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/1 μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette.

For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Glucose-6-Phosphate/Phosphate Translocators The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for GP/PT are presented by Kammerer et al. (1998) *Plant Cell* 10:105–117.

What is claimed is:

1. An isolated polynucleotide comprising:
    (a) a nucleotide sequence encoding a polypeptide having glucose-6-phosphate/phosphate translocator activity, wherein the amino acid sequence of the polypeptide and the amino acid sequence of SEQ ID NO:4 have at least 86% sequence identity based on the Clustal alignment method, or
    (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of SEQ ID NO:4 have at least 90% sequence identity based on the Clustal alignment method.

3. The polynucleotide of claim 1, wherein the amino acid sequence of the polypeptide and the amino acid sequence of SEQ ID NO:4 have at least 95% sequence identity based on the Clustal alignment method.

4. The polynucleotide of claim 1, wherein the nucleotide sequence comprises the nucleotide sequence of SEQ ID NO:3.

5. The polynucleotide of claim 1, wherein the polypeptide comprises the amino acid sequence of SEQ ID NO:4.

6. A recombinant DNA construct comprising the polynucleotide of claim 1 operably linked to a regulatory sequence.

7. A method for transforming a cell comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 1.

11. A seed comprising the recombinant DNA construct of claim 1.

12. A vector comprising the polynucleotide of claim 1.

* * * * *